United States Patent [19]

Cowen

[11] Patent Number: 5,063,914

[45] Date of Patent: Nov. 12, 1991

[54] PENILE PROSTHESIS

[75] Inventor: Timothy B. Cowen, Andover, Minn.

[73] Assignee: Mentor Corporation, Minneapolis, Minn.

[21] Appl. No.: 530,339

[22] Filed: May 30, 1990

[51] Int. Cl.[5] ............................................. A61F 2/26
[52] U.S. Cl. ..................................................... 128/79
[58] Field of Search ......................................... 128/79

[56] References Cited

U.S. PATENT DOCUMENTS

| 4,424,807 | 1/1984 | Evans, Sr. | 128/79 |
| 4,875,472 | 10/1989 | Levius | 128/79 |
| 4,881,530 | 11/1989 | Trick | 128/79 |

Primary Examiner—Cary E. O'Connor
Attorney, Agent, or Firm—Hugh D. Jaeger

[57] ABSTRACT

An apparatus for the treatment of male impotence. The apparatus has a cylinder of a biocompatible polymer which is implanted in the corpus cavernosum of the penis. The cylinder is attached at its proximal end to a base mount which is implanted in the pelvic area. In the flaccid state, the cylinder is empty and limp, and a spring within the cylinder folds the cylinder wall in upon itself to decrease its effective length. Fluid is pumped into the cylinder causing it to stiffen in the erect state. The effective length of the cylinder is increased by the addition of the fluid which compresses the internal spring and unfolds the cylinder. In this manner, the length of the penis is increased from the flaccid to the erect state.

4 Claims, 4 Drawing Sheets

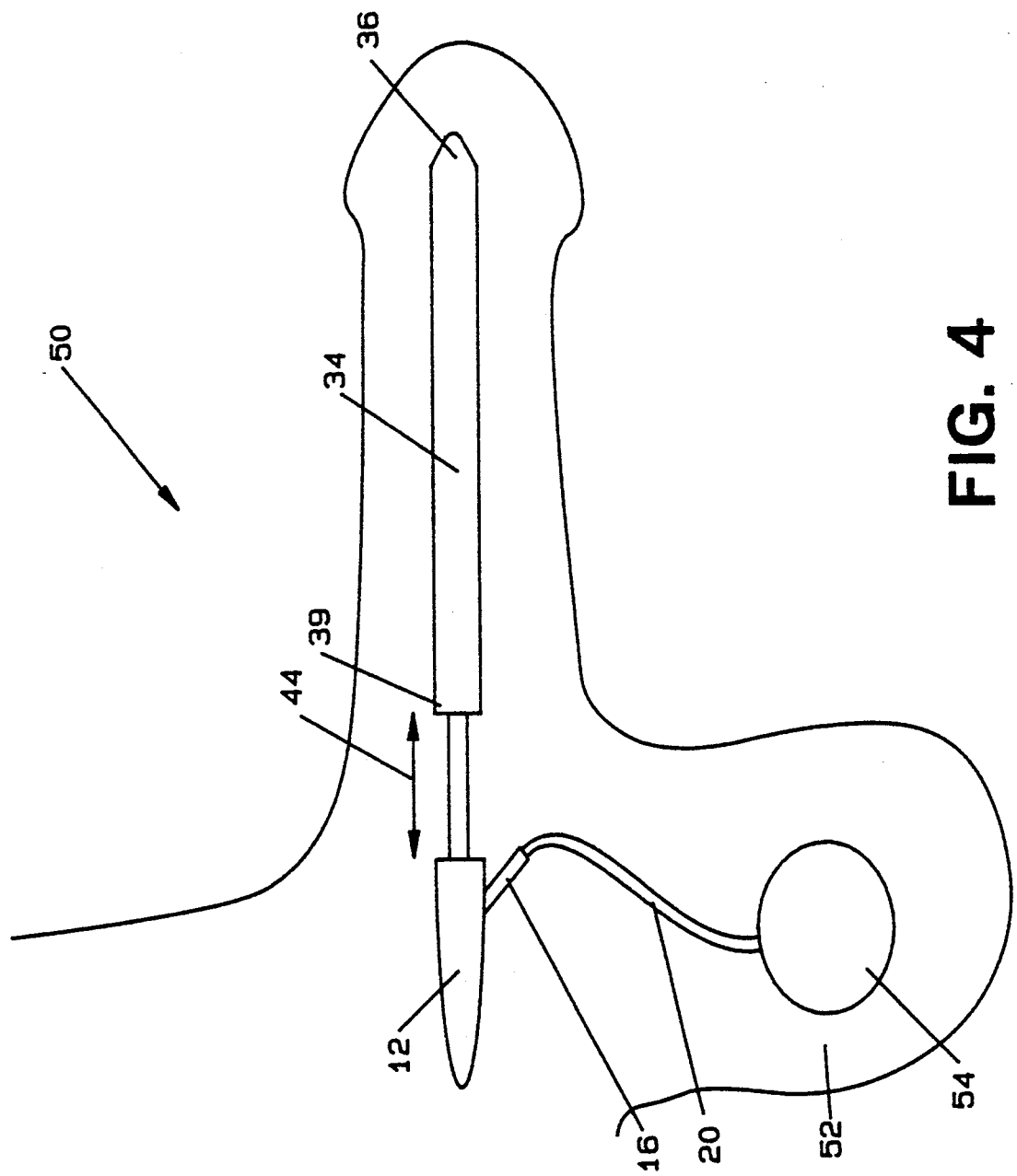

PENILE PROSTHESIS

CROSS REFERENCE TO CO-PENDING APPLICATIONS

This application is related to Ser. No. 07/522,821, filed May 14, 1990, entitled "Corpus Cavernosum Implant Device", assigned to the assignee of the present invention.

BACKGROUND OF THE INVENTION

1. Field of the Invention

The present invention relates generally to implantable medical devices, and more specifically, relates to implantable medical devices for the treatment of male impotence.

2. Description of the Prior Art

Implantable cylinders for the treatment of male impotence have been in use for some time. The more sophisticated of these devices employ fluid systems whereby the cylinder may be evacuated to produce the flaccid state and inflated to produce the erect state.

An early patent disclosing such an implantable system is U.S. Pat. No. 4,009,711, issued to Uson et al., which uses a pair of inflatable cylinders implanted in a corpus cavernosum of the penis. Each of the cylinders include a non-distensible portion of a semi-rigid material to be implanted into the root end of the corpus cavernosum and a pendulous, distensible body portion. The distensible body portion or inflatable cylinder is connected by tubing to a fluid reservoir located in the scrotal sac, and a check valve is provided to control the flow of fluid between the reservoir and the inflatable cylinder. A similar device is disclosed in U.S. Pat. No. 4,235,227, issued to Yamanaka.

A more recent design of a prosthesis is found in U.S. Pat. No. 4,726,360 which discloses that each inflatable tube can be encased in an outer sleeve which is permanently filled with a fluid, thereby providing an outer, annular pressure chamber. The distensible cylinders described in these references are formed of silicone rubber and have limited elasticity to avoid girth expansion of the cylinders upon inflation. This limited elasticity of the cylinders, however, undesirably limits the longitudinal growth from flaccid state to erect state.

U.S. Pat. No. 4,730,607, issued to Fischell suggests that the longitudinal growth of a stiffener cylinder can be improved by providing several bellow-type folds in the cylinder. The bellow-type folds are described as having sufficient depth to increase the extendibility of the cylinder from 6 percent to about 13 percent. Fischell teaches that these folds should be located near the base to function as a strain relief in the flaccid state.

Even though the Fischell device is a minimal attempt at providing an extendible stiffening cylinder, the total length increase in the prior art devices is very small compared to that which occurs under normal conditions from flaccid to erect state.

SUMMARY OF THE INVENTION

The present invention overcomes the difficulties found in the prior art by providing an inflatable stiffening cylinder which yields a substantial increase in length from the deflated or flaccid state to the inflated or erect state. This increase is achieved by using a cylinder of a flexible, biocompatible polymer which is folded in upon itself in the deflated state. This folding is ensured by an internal spring coupled to the cylinder such that the spring is in the relaxed state when the cylinder is folded in. As the cylinder is inflated, the fluid pressure causes the cylinder to unfold to increase its volume. In doing so, the internal spring is caused to compress thereby storing energy to refold the cylinder upon deflation.

The increase in length experienced in the inflated state is caused by an effective increase in the volume (i.e. the effective length) of the cylinder. Therefore, the extendibility is not dependent upon the elasticity of the polymer used to fabricate the cylinder. This permits a polymer to be chosen that has the proper elasticity to achieve the desired stiffening, longitudinal collapse strength, and control of girth in the inflated condition.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
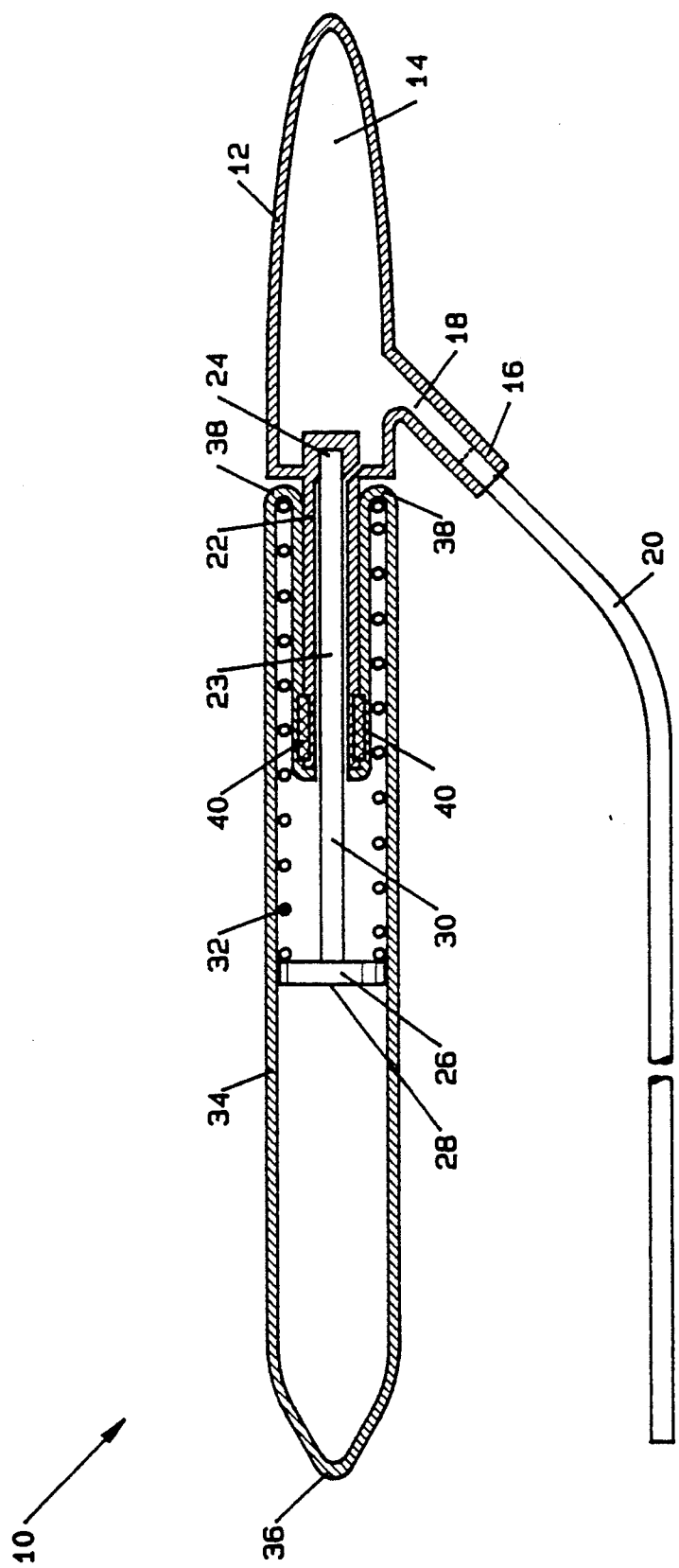
FIG. 1 is a plan view of an inflatable stiffening cylinder employing the present invention shown in the deflated state.

FIG. 1 is a plan view of an implantable prosthesis 10 in the deflated state employing the present invention. Base mount 12 is adapted to be implanted in the pelvic area of the patient. It is molded of an implantable material such as silicone rubber. It has a molded fluid port 16 which has an inner lumen 18 in fluid communication with the inner lumen 14 of base mount 12. Flexible tubing 20 is in fluid communication with inner lumen 18 of molded fluid port 16. The operation of these fluid paths is described in more detail below.

Also molded on to base mount 12 is base cylinder 22 which provides for attachment of inflatable stiffening cylinder 34. Base cylinder 22 contains central lumen. Inflatable stiffening cylinder 34 is fabricated from a flexible and implantable polymer. It is sealingly attached along the distal end of base cylinder 22 at point 40. Inflatable stiffening cylinder 34 has conical point 36 at its distal tip.

Disposed within base cylinder 22 is a spring retainer 30 having a retaining disc 26 attached to its distal end. The proximal end of the spring retainer 30 is fixedly attached to the proximal end of base cylinder 22 at point 24, as shown. The interior of inflatable stiffening cylinder 34 is in fluid communication with inner lumen 14 of base mount 12 through central lumen 23 within spring retainer 30. Central lumen 23 exits to the interior of inflatable stiffening cylinder 34 through aperture 28.

Spring 32 is shown in the relaxed state. This occurs when inflatable stiffening cylinder 34 is deflated. The distal end of spring 32 is positioned against retaining disc 26 of spring retainer 30. The proximal end of spring 32 exerts force against point 38 of inflatable stiffening cylinder 34 which is folded in on itself at point 38. In the deflated state, inflatable stiffening cylinder 34 is shortened by the folding in from point 38 (i.e. the point at which spring 32 exerts its force) to the point 40 (i.e. the point at which inflatable stiffening cylinder 34 is attached). This distance corresponds to the distance over which inflatable stiffening cylinder 34 is folded in on itself (i.e. from point 38 to point 40). This distance is determined by the length of base cylinder 22 and the properties of spring 32.

Figure 2:
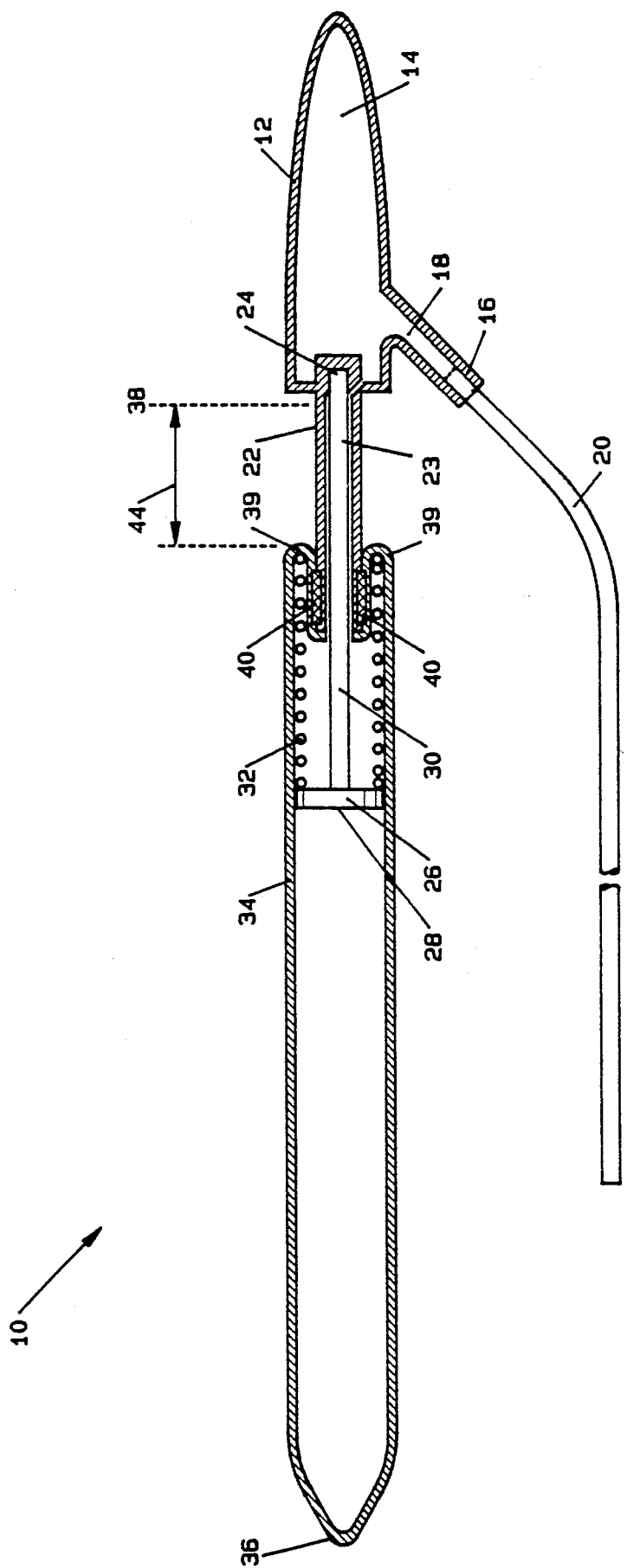
FIG. 2 is a plan view of the inflatable stiffening cylinder of FIG. 1 shown in the inflated state.

FIG. 2 is a plan view of the implantable prosthesis 10 of FIG. 1 shown in the inflated or erect state wherein referenced elements are as described above. To be inflated, a fluid such as sterile saline solution is forced under pressure from a reservoir (not shown into flexible tubing 20. The fluid flows through inner lumen 14 of base mount 12 and into central lumen 23 of spring retainer 30. Inflatable stiffening cylinder 34 is filled from the fluid as it exits aperture 28 of retaining disc 26.

As inflatable stiffening cylinder 34 is filled, its effective length is increased by an unfolding of the cylinder wall disposed against the proximal end of spring 32. As the wall of inflatable stiffening cylinder 34 is unfolded, spring 32 is compressed between retaining disc 26 and the wall of inflatable stiffening cylinder 34. Upon filling of inflatable stiffening cylinder 34, spring 32 becomes compressed against point 39 of the cylinder wall. The effective length of the inflatable stiffening cylinder 34 is extended by distance 44 which represents the difference between the projection on base cylinder 22 of point 38 and the similar projection of point 39. The result is that in the fully inflated state, inflatable stiffening cylinder 34 is only folded in on itself from point 39 to point 40 (i.e. the point of attachment of inflatable stiffening cylinder 34 to base cylinder 22).

Figure 3:
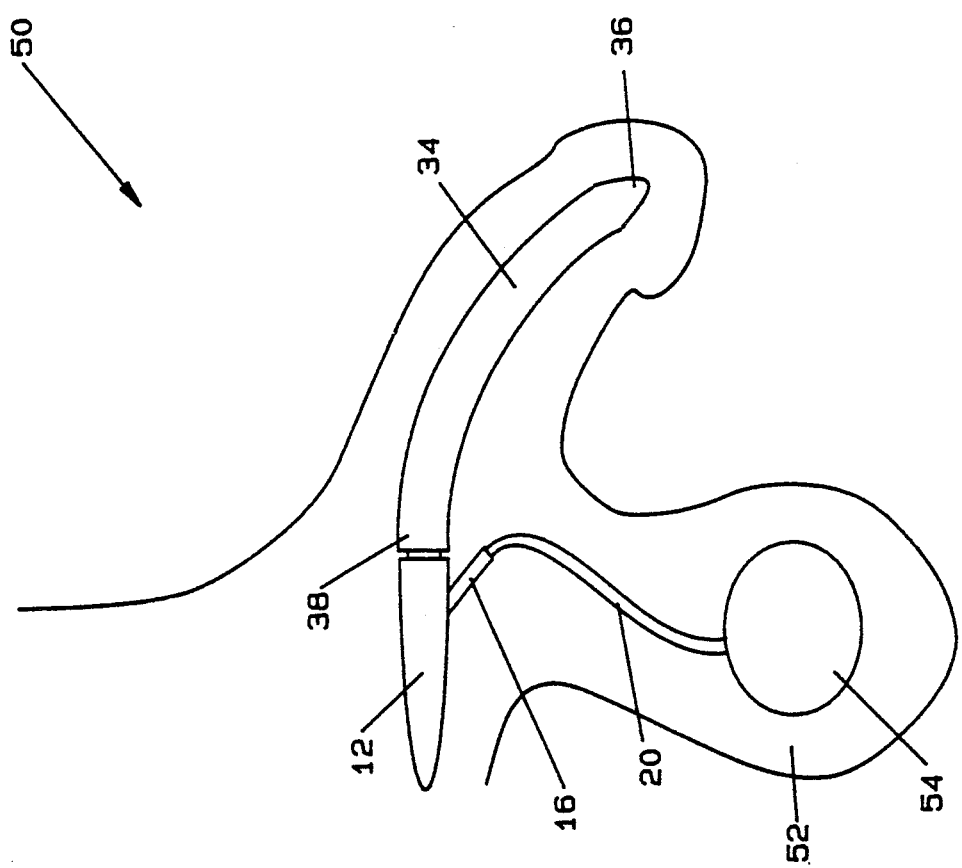
FIG. 3 is a schematic view of an implant of a system employing the present invention shown in the flaccid state; and, FIG. 4 is a schematic view of the implant of FIG. 3 shown in the erect state.

FIG. 3 is a schematic view of the prosthetic device 10 in the flaccid state after implantation in the patient. As can be seen, base mount 12 is implanted in the pelvic area and inflatable stiffening cylinder 34 is implanted in penis 50. A reservoir 54, implanted in scrotum 52, holds the fluid which is manually pumped into inflatable stiffening cylinder 34 through flexible tubing 20 and molded fluid port 16 using known techniques. In the flaccid state, inflatable stiffening cylinder 34 is maximally folded in and the proximal end of spring 32 is disposed against point 38 of inflatable stiffening cylinder 34 (see also FIG. 1).

FIG. 4 is a schematic view of the implant of FIG. 3 shown in the inflated (i.e. erect) state wherein all reference numerals are as previously described. It can be readily seen that the effective length of inflatable stiffening cylinder 34 and hence penis 50 is increased by distance 44 as explained above.

The present invention has been described with reference to the illustrated and presently preferred embodiments. However, those of skill in the art will be able to apply the teachings found herein to yet other embodiments without departing from the scope of the claims hereto attached.

I claim:
1. A penile prosthesis comprising:
   a. a base mount;
   b. an inflatable stiffening cylinder of flexible body implantable material;
   c. a source of pressurized fluid in fluid communication with said inflatable stiffening cylinder; and,
   d. means coupled to said inflatable stiffening cylinder for decreasing the effective length of said inflatable stiffening cylinder whenever said pressurized fluid is removed from said inflatable stiffening cylinder, including spring means for encouraging said inflatable stiffening cylinder to fold over.

2. An apparatus according to claim 1 wherein said spring means is relaxed whenever said pressurized fluid is removed from said inflatable stiffening cylinder and compressed whenever said pressurized fluid fills said inflatable stiffening cylinder.

3. An apparatus according to claim 2 wherein said spring means is disposed upon a spring retainer.

4. An apparatus according to claim 3 wherein said spring retainer contains a lumen which is in fluid communication with said inflatable stiffening cylinder and said source of pressurized fluid.

* * * * *